United States Patent [19]

Ledley

[11] 4,417,967

[45] Nov. 29, 1983

[54] GROOVED GEL

[75] Inventor: Robert S. Ledley, Silver Spring, Md.

[73] Assignee: Georgetown University, Washington, D.C.

[21] Appl. No.: 324,447

[22] Filed: Nov. 24, 1981

[51] Int. Cl.$^3$ .................. B01D 57/02; C25B 7/00; C25D 13/00

[52] U.S. Cl. .................. 204/180 G; 204/180 R

[58] Field of Search .................. 204/180 G

[56] References Cited

U.S. PATENT DOCUMENTS

| | | | |
|---|---|---|---|
| 3,616,456 | 10/1971 | Valmet | 204/180 G |
| 3,767,560 | 10/1973 | Elevitch | 204/299 |
| 3,773,645 | 11/1973 | Nees et al. | 204/180 G |
| 3,773,646 | 11/1973 | Mandle et al. | 204/299 |
| 3,791,950 | 2/1974 | Allington | 204/180 G |
| 3,879,280 | 4/1975 | Peterson et al. | 204/299 |
| 3,888,759 | 6/1975 | Elson et al. | 204/299 |
| 3,932,229 | 1/1976 | Grandine | 204/180 G |
| 4,094,759 | 6/1978 | Ruhenstroth-Bauer et al. | 204/180 G |
| 4,130,471 | 12/1978 | Grumbaum | 204/180 G |
| 4,181,594 | 1/1980 | Rizk et al. | 204/180 G |
| 4,207,166 | 6/1980 | Dahms | 204/299 R |

FOREIGN PATENT DOCUMENTS 1274074  1/1968  Fed. Rep. of Germany ... 204/180 G
1455644  11/1976  United Kingdom .

OTHER PUBLICATIONS

O'Farrell, "High Resolution Two-Dimensional Electrophoresis of Proteins," *J. Biol. Chem.*, vol. 250, No. 10 (5/25/75), pp. 4007–4021.

Rosenfeld, "The Great Protein Hunt," *Science*, Jan.-/Feb. 1981, pp. 64–67.

*Primary Examiner*—Arthur P. Demers
*Attorney, Agent, or Firm*—Oblon, Fisher, Spivak, McClelland & Maier

[57] ABSTRACT

A grooved gel arrangement comprises a base portion having grooves extending in a longitudinal direction thereof, a gel disposed on the grooved portion and filling in the grooves, and a top portion disposed on top of the base portion, with the gel sandwiched therebetween. When protein is applied to the gel and is subjected to an electrophoretic procedure, diffusion of the protein is substantially eliminated.

20 Claims, 3 Drawing Figures

GROOVED GEL

BACKGROUND OF THE INVENTION

1. Field of the Invention

The present invention relates to a grooved gel, and more specifically to a grooved gel arrangement wherein distortions and spreading (diffusion) of proteins within the gel are eliminated or at least minimized.

2. Description of Prior Art

The human body contains proteins which are remarkably diverse in size, architecture and biological responsibility. They range in molecular weight from a few thousand to more than a million. They may be stretched into long, strong fibers or coiled into compact globules. They exist in a variety of different forms, such as: structural proteins, connective-tissue proteins, contractile muscle proteins, enzymes, hormones, antibodies, transport molecules (such as the hemoglobin which carries oxygen to the cells), storage proteins, cell-surface receptors, and the like.

One of the traditional methods for separating proteins for the purpose of identification is electrophoresis, which simply means "carried by electricity". Proteins from, for example, a blood or urine sample, appropriately prepared, can be separated in an electrical field because each different type of protein is carried along at a slightly different speed, depending on the net electrical charge of a given molecule. This method, one-dimensional electrophoresis, has proven to be an extremely powerful scientific tool.

In the mid 1970s, two-dimensional techniques for separating proteins were developed. One such technique was designated "gel electrophoresis", and comprises a technique which differentiates proteins moving through a gel into clearly delineated bands which can be identified as specific proteins or groups of proteins. The method separates proteins moving in one direction by their electrical charge into single rows. Then, the gel is turned on its side, and a detergent is added to interact electrically with the proteins, causing them to move in a second direction, by which movement in the second direction they are sorted out by size. Moreover, when the two-dimensional gel is stained with a dye, the result is a grid-like series of protein "spots", the columns being separated horizontally by their electrical charge, and vertically by size. Such a "protein map" can separate a great many more proteins from a sample than is possible with one-dimensional electrophoresis.

Gels utilized in the latter manner can then be scanned, the gel being divided into a very large number (for example, one or two million) tiny squares, each square being examined and analyzed by well-known computer information processing techniques. Once each square is analyzed in detail, the corresponding data can be stored for future recall, enhancement, and display. Moreover, the density data can be converted into color differences for easier discrimination and viewing on a computerized display. In addition, the "background noise", typically present in such scan-derived information, can be filtered out by a computer system, and distortions in the gel itself can also be corrected. A detailed treatment of such two-dimensional electrophoretic procedures is set forth in "High Resolution Two-Dimensional Electrophoresis of Proteins", by Patrick H. O'Farrell, *The Journal of Biological Chemistry*, Volume 250, No. 10 (May 25, 1975), pages 4007–4021.

It should be recognized that, for the purpose of gel analysis using computerized scanning, it is important that resolution be minimized to the greatest extent possible. On the other hand, attempts to minimize resolution, have in the past, been thwarted by the occurrence of the phenomenon known as diffusion (spreading). That is, during the first-dimensional phase of the electrophoretic procedure, the proteins are distributed latitudinally across the gel, and then, during the second-dimensional phase of the procedure, the proteins are distributed longitudinally through the gel along respective paths or channels. During the latter procedure, diffusion (spreading) of the proteins can take place, thus providing a distorted distribution of the proteins, and this adversely affects the resolution which can be achieved by the gel scanning procedure.

In addition, during the fabrication of gels, the physical gel itself often becomes distorted, and this adversely affects the process by means of which the proteins are distributed latitudinally and longitudinally within the gel during the electrophoretic procedure. This amounts to a further cause of adverse diffusion (spreading) of the protein within the gel, thus further adversely affecting the data derived from scanning of the gel during the computer scanning phase of operation.

SUMMARY OF THE INVENTION

The present invention relates to a grooved gel, and more particularly to a grooved gel arrangement in which distortion and spreading (diffusion) of protein spots within the gel are eliminated or at least minimized. More specifically, according to the invention, a plastic backing for holding the gel is formed with grooves disposed in it, so that, when the gel is disposed on the plastic backing, the gel fills in the grooves in the plastic backing, thus forming a grooved gel arrangement.

As a result of utilization of a grooved plastic backing during the procedure of fabricating the gel, distortion of the physical gel itself is prevented or at least minimized. This, in turn, prevents diffusion (spreading) of protein, during the electrophoretic procedure, and thus resolution is reduced and minimized.

Once the gel is formed on the grooved plastic backing, a glass or plastic top cover or plate can be placed over the gel, and the gel can be appropriately arranged so that a conventional electrophoretic procedure can be carried out. During the latter procedure, proteins which would otherwise tend to diffuse or spread during their dispersion longitudinally along the gel will not do so, thus preventing distorted results from being obtained during the computerized scanning of the gel.

Therefore, it is a primary object of the present invention to provide a grooved gel, and more particularly a grooved gel arrangement.

It is an additional object of the present invention to provide a grooved gel arrangement in which distortion of the physical gel itself, which would otherwise be introduced during the fabrication phase, is prevented.

It is an additional object of the present invention to provide a grooved gel arrangement in which diffusion (spreading) of proteins during an electrophoretic procedure is precluded or minimized.

The above and other objects that will hereinafter appear, and the nature of the invention, will be more clearly understood by reference to the following description, the appended claims, and the accompany drawings.

DETAILED DESCRIPTION

The invention of the application will now be more fully described with reference to the various figures of the drawings.

Figure 1:
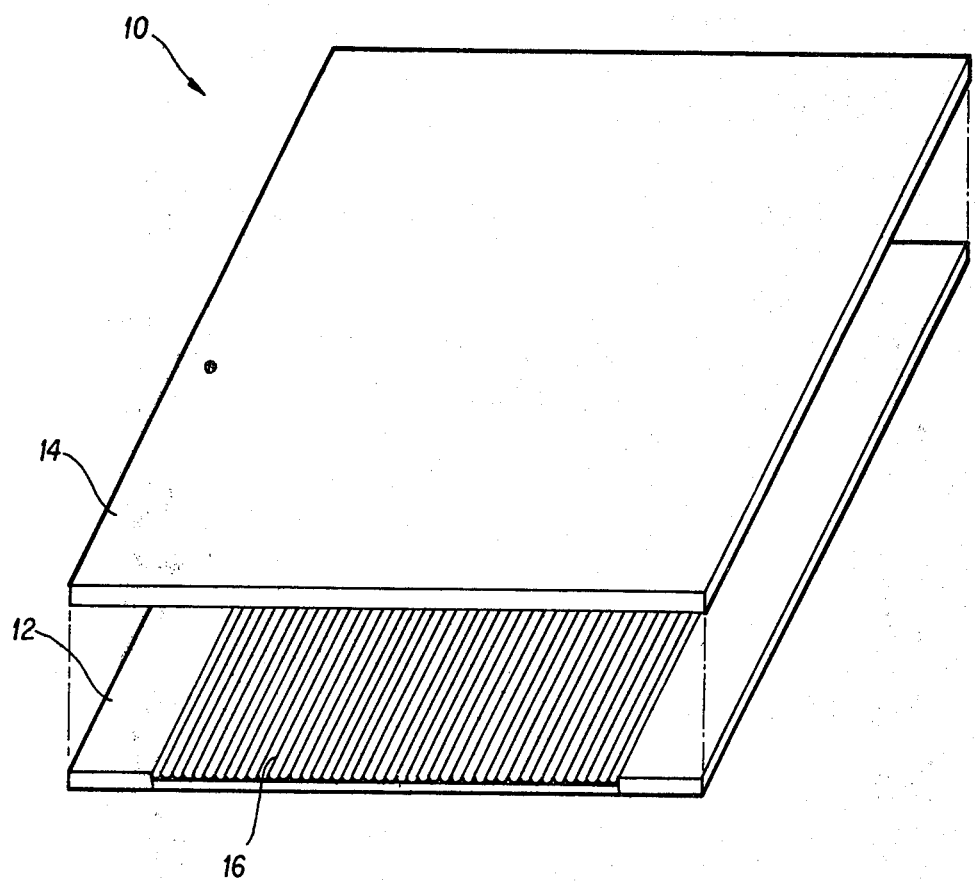
FIG. 1 is a perspective view of a grooved gel arrangement according to the present invention.

As seen in FIG. 1, which is a perspective view of the grooved gel arrangement of the present invention, the grooved gel arrangement 10 basically comprises a grooved base plate 12 and a top plate 14. A given portion 16 of the base plate 12 has grooves disposed longitudinally for receiving a gel disposed thereon. Preferably, the grooves are arranged in a very fine array, with the spacing between the grooves being on the order of fraction of a millimeter.

The process of constructing a grooved gel arrangement according to the present invention will now be described with reference to FIG. 2, which is a top view of the grooved base plate 12. The grooved base plate 12 is preferably made of plastic or other similar non-conductive material and, as previously mentioned, contains a portion 16 having grooves disposed thereon with very close spacing. With the grooved base plate positioned in a horizontal posture, a gel is disposed thereon in such a way that the gel fills in the grooved spaces contained in the portion 16 of the base plate 12.

Figure 3:
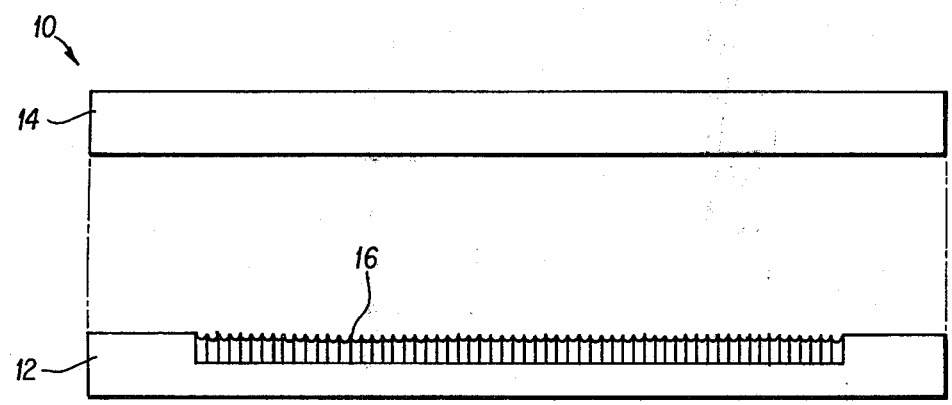
FIG. 3 is a front view of the grooved gel arrangement of the present invention.

FIG. 3 is a front view of the grooved gel arrangement of the present invention. As seen therein, once the gel is disposed on the grooved portion 16, it fills in the grooves, thus forming a uniform, stable and well-supported grooved gel structure on the base plate 12.

As further shown in FIGS. 1 and 3, a top plate 14 is then positioned on top of the grooved base plate 12 so as to sandwich the gel therebetween. The top plate 14 is, preferably, plastic, glass, or other non-conductive and transparent material.

Needless to say, some sort of access means or opening (not shown) must be provided in the grooved gel arrangement so that, once the top plate 14 is positioned on the grooved base plate 12, with the gel sandwiched therebetween in the grooved portion 16, protein samples can be inserted at a given point in the portion 16. Once such protein samples are inserted into the grooved portion 16, the electrophoretic procedure can be carried out. That is to say, during the first phase, proteins can be separated according to isoelectric point by isoelectric focusing in the first dimension, and then, during the second phase, proteins are separated according to molecular weight by electrophoresis in the second dimension.

Figure 2:
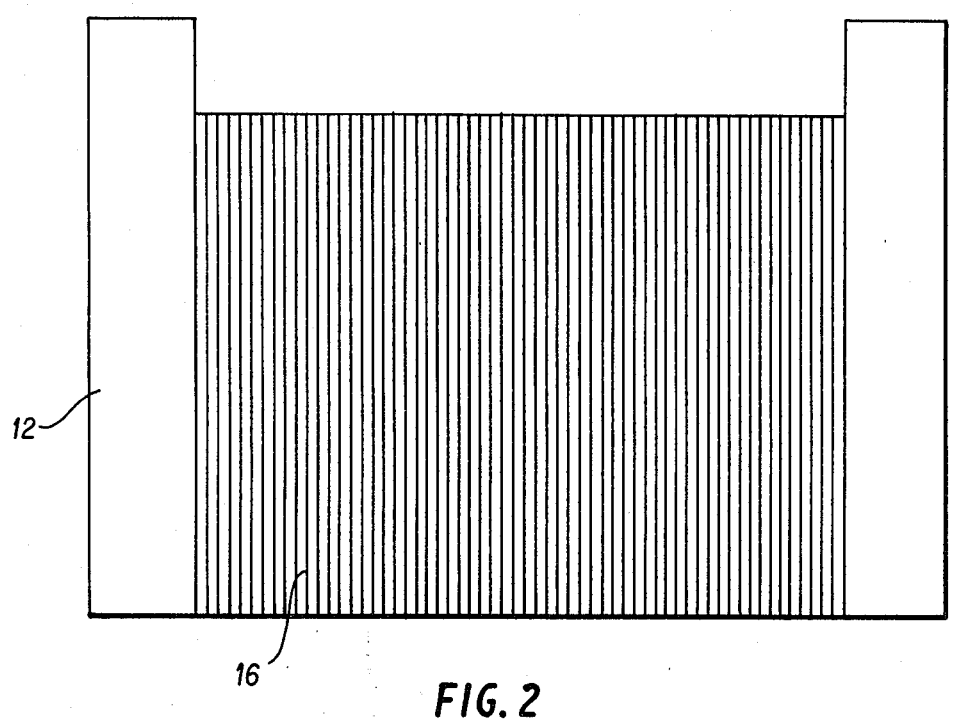
FIG. 2 is a top view of the grooved base plate utilized in the grooved gel arrangement of the present invention.

More specifically, as previously mentioned, during the first phase, gel electrophoresis is carried out by means of applying an electric field latitudinally across the gel (that is, in a direction from left to right in FIGS. 1–3). This differentiates proteins moving through the gel into clearly delineated bands which can be identified as specific proteins or groups of proteins. The technique separates proteins moving in the single direction, by virtue of their electrical charge, into single rows.

Then, the gel is turned on its side, and a further electrophoretic procedure is carried out (for example, a detergent can be added to interact electrically with the proteins in each of the single rows). The proteins in each row are caused to move in a second direction, longitudinally across the gel (that is, from bottom to top in FIG. 2), and the proteins are, in this manner, sorted out by size.

Finally, as mentioned previously, if the two-dimensional gel is then stained with a dye, the result is a grid-like series of protein "spots", with the columns separated horizontally by electrical charge, and vertically by size. This "protein map" can then be submitted to a computerized scanning procedure, by means of which a scanner, connected to a computer system, can scan the surface of the grooved gel (in a manner similar to the way in which a television is raster-scanned) so as to develop data pertaining to the "protein map". With reference to FIG. 3, this scanning can take place by virtue of the transparency of the top plate 14 (which, as previously mentioned, is preferably of plastic, glass or other transparent, non-conductive material).

It is to be further noted that, during the electrophoretic procedure, and specifically during the second phase thereof, proteins are travelling longitudinally along the grooved portion 16 (FIG. 2) of the base plate 12 (from bottom to top, as seen in FIG. 2). Since the grooved base plate 12 was employed during the fabrication procedure in forming the gel, the gel will be of a uniform construction, and will have very little or no physical distortion. This serves to preclude diffusion or spreading of the proteins as they travel longitudinally along the grooved portion 16.

In addition, by virtue of the presence of the grooves in the grooved portion 16, during the second phase of the electrophoretic procedure, the natural diffusion or spreading of the proteins as they travel longitudinally along the grooved portion 16 will be minimized or eliminated by virtue of the chanellizing effect of the grooves contained in the grooved portion 16. That is to say, the walls of the grooves contained in the grooved portion 16 act to inhibit latitudinal diffusion (spreading) of the protein as it is travelling in a longitudinal direction (from bottom to top in FIG. 2) along the grooved portion 16 of the base plate 12.

While preferred forms and arrangements have been shown in illustrating the invention, it is to be clearly understood that various changes in detail and arrangement may be made without departing from the spirit and scope of this disclosure.

What is claimed is:

1. A grooved gel arrangement suitable for two-dimensional gel electrophoresis comprising:

a base portion having a latitudinal direction and a longitudinal direction, and including a grooved portion having grooves extending in said longitudinal direction for substantially the entire longitudinal width of said plate, said grooves being of such spacing that said grooves inhibit latitudinal spreading of protein which has been separated in said latitudinal direction when said protein travels in said longitudinal direction along said grooves;

a gel disposed on said grooved portion and filling in said grooves thereof; and a top portion disposed on top of said base portion, with said gel sandwiched therebetween.

2. The arrangement of claim 1, wherein said base portion comprises a non-conductive material.

3. The arrangement of claim 2, wherein said non-conductive material is plastic.

4. The arrangement of claim 1, wherein said top portion is made of a non-conductive material.

5. The arrangement of claim 4, wherein said non-conductive material is glass.

6. The arrangement of claim 4, wherein said non-conductive material is plastic.

7. The arrangement of claim 1, wherein said top portion comprises a transparent material.

8. The arrangement of claim 7, wherein said transparent material is glass.

9. The arrangement of claim 7, wherein said transparent material is plastic.

10. The arrangement of claim 1, wherein said grooves are spaced less than 1 millimeter apart.

11. The arrangement of claim 10, wherein said base portion comprises a non-conductive material.

12. The arrangement of claim 11, wherein said non-conductive material is plastic.

13. The arrangement of claim 10, wherein said top portion is made of a non-conductive material.

14. The arrangement of claim 13, wherein said non-conductive material is glass.

15. The arrangement of claim 13, wherein said non-conductive material is plastic.

16. The arrangement of claim 10, wherein said top portion comprises a transparent material.

17. The arrangement of claim 16, wherein said transparent material is glass.

18. The arrangement of claim 16, wherein said transparent material is plastic.

19. A method of conducting two-dimensional gel electrophoresis, which comprises:

conducting gel electrophoresis in a latitudinal direction, whereby a protein mixture is separated into components in said latitudinal direction; and conducting gel electrophoresis of said components in a longitudinal direction through a gel disposed on a plate having grooves extending for substantially the entire longitudinal direction of said plate, said grooves being of such spacing that said grooves inhibit latitudinal spreading of said components when said protein mixture travels in said longitudinal direction along said grooves.

20. The method of claim 19, wherein said spacing is less than 1 millimeter.

* * * * *

UNITED STATES PATENT AND TRADEMARK OFFICE
CERTIFICATE OF CORRECTION

PATENT NO. : 4,417,967
DATED : November 29, 1983
INVENTOR(S) : Ledley

It is certified that error appears in the above-identified patent and that said Letters Patent is hereby corrected as shown below:

First page, under the section entitled "Other Publications," fourth line, change "Science," to -- Science 81, --;

Column 2, line 67, change "accompany" to -- accompanying --;

Column 3, line 23, change "fraction" to -- fractions --;

Column 4, line 39, change "chanellizing" to -- channelizing --.

Signed and Sealed this

Thirtieth Day of October 1984

[SEAL]

Attest:

Attesting Officer

GERALD J. MOSSINGHOFF

Commissioner of Patents and Trademarks